United States Patent
Wolfe

(10) Patent No.: US 7,632,014 B2
(45) Date of Patent: Dec. 15, 2009

(54) LARGE X-RAY DETECTOR VARIABLE CENTERING FOR ANGULATION ENHANCEMENT

(75) Inventor: Albert Wolfe, Kingwood, TX (US)

(73) Assignee: General Electric Company, Schenectady, NY (US)

(*) Notice: Subject to any disclaimer, the term of this patent is extended or adjusted under 35 U.S.C. 154(b) by 180 days.

(21) Appl. No.: 11/828,183

(22) Filed: Jul. 25, 2007

(65) Prior Publication Data
US 2009/0028293 A1 Jan. 29, 2009

(51) Int. Cl.
*A61B 6/08* (2006.01)
(52) U.S. Cl. .................................... 378/205
(58) Field of Classification Search ............ 378/11, 378/17, 19, 205
See application file for complete search history.

(56) References Cited

U.S. PATENT DOCUMENTS

| 4,324,978 A * | 4/1982 | Kalender et al. ............ 378/4 |
| 4,991,189 A * | 2/1991 | Boomgaarden et al. ........ 378/4 |
| 6,580,777 B1 * | 6/2003 | Ueki et al. .................. 378/17 |
| 2004/0179650 A1 * | 9/2004 | Hoffman .................. 378/98.8 |
| 2004/0258195 A1 * | 12/2004 | Hara ............................ 378/11 |

\* cited by examiner

*Primary Examiner*—Chih-Cheng G Kao
(74) *Attorney, Agent, or Firm*—Peter Vogel, Esq.; William Baxter, Esq.; Michael G. Smith, Esq.

(57) ABSTRACT

Systems, methods and apparatus are provided for angulation enhancement. An X-ray system comprising X-ray detector and X-ray source disposed at different ends of the X-ray system. An apparatus shifts a beam field produced by the X-ray source towards the edge of the X-ray detector whereby a large X-ray detector on a vascular X-ray system can be utilized to image smaller anatomy at extremes angles.

23 Claims, 12 Drawing Sheets

LARGE X-RAY DETECTOR VARIABLE CENTERING FOR ANGULATION ENHANCEMENT

FIELD OF THE INVENTION

This invention relates generally to X-ray systems having large X-ray detectors and the ability to image anatomy at extreme angles, and more particularly to the centering of a beam field for angulation enhancement.

BACKGROUND OF THE INVENTION

In medical imaging, flat detectors vary widely based on the medical procedure, different sizes and formats optimize patient access and matching to the respective examination area such as for cardiological applications, angiographic applications, fluoroscopy examinations or vascular applications, and radiography. One important criterion in selecting the detector size is the ease of access to the patient during the imaging cycle. It is not possible to perform certain examinations using a detector of a different size, since in this case is not possible for sufficiently close access to the patient to be achieved. Since each detector size is only suitable for certain procedures, various size detectors are manufactured so as to cover all types of examinations occurring in practice. While different sizes enable numerous requirements to be met, it also results in considerable cost increases to both manufacturers and purchasers of the imaging equipment.

Various techniques have been proposed to reduce the number of detectors needed in a medical facility. For small X-ray detectors, techniques such as mathematical extrapolation, two position data acquisition scheme in which an object is translated and rotated relative to a stationary source-detector configuration, and mounting a patient on a turntable that may be displaced and rotated have been proposed viable methods for increasing the detector's imaging capabilities. In the case of larger detectors, especially for scanning anatomy more suited for a smaller detector, it has been suggested to place the larger detector far from the patient during longitudinally angulated views. However, the placement of the detector far from the patient compromises image quality and increases dosage.

For the reasons stated above, and for other reasons stated below which will become apparent to those skilled in the art upon reading and understanding the present specification, there is a need in the art for an X-ray system that can be utilized to image larger and smaller anatomies with a single X-ray detector.

BRIEF DESCRIPTION OF THE INVENTION

The above-mentioned shortcomings, disadvantages and problems are addressed herein, which will be understood by reading and studying the following specification.

In one aspect, an X-ray system is disclosed for angulation enhancement. The X-ray imaging system comprises an X-ray detector and an X-ray source disposed at different ends of the X-ray system. A means is provided for shifting a beam field produced by the X-ray source towards the edge of the X-ray detector.

In another aspect, a flat panel detector arranged on one or more rails is disclosed. The rails are utilized to move or shift the X-ray detector so as to cause the beam field to be produced at the edge of the detector. The shifting of the detector through the rail has no effect on the geometry or centering of the beam.

In yet another aspect, the X-ray detector is held stationary while the beam field is shifted off the central axis by a collimator.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
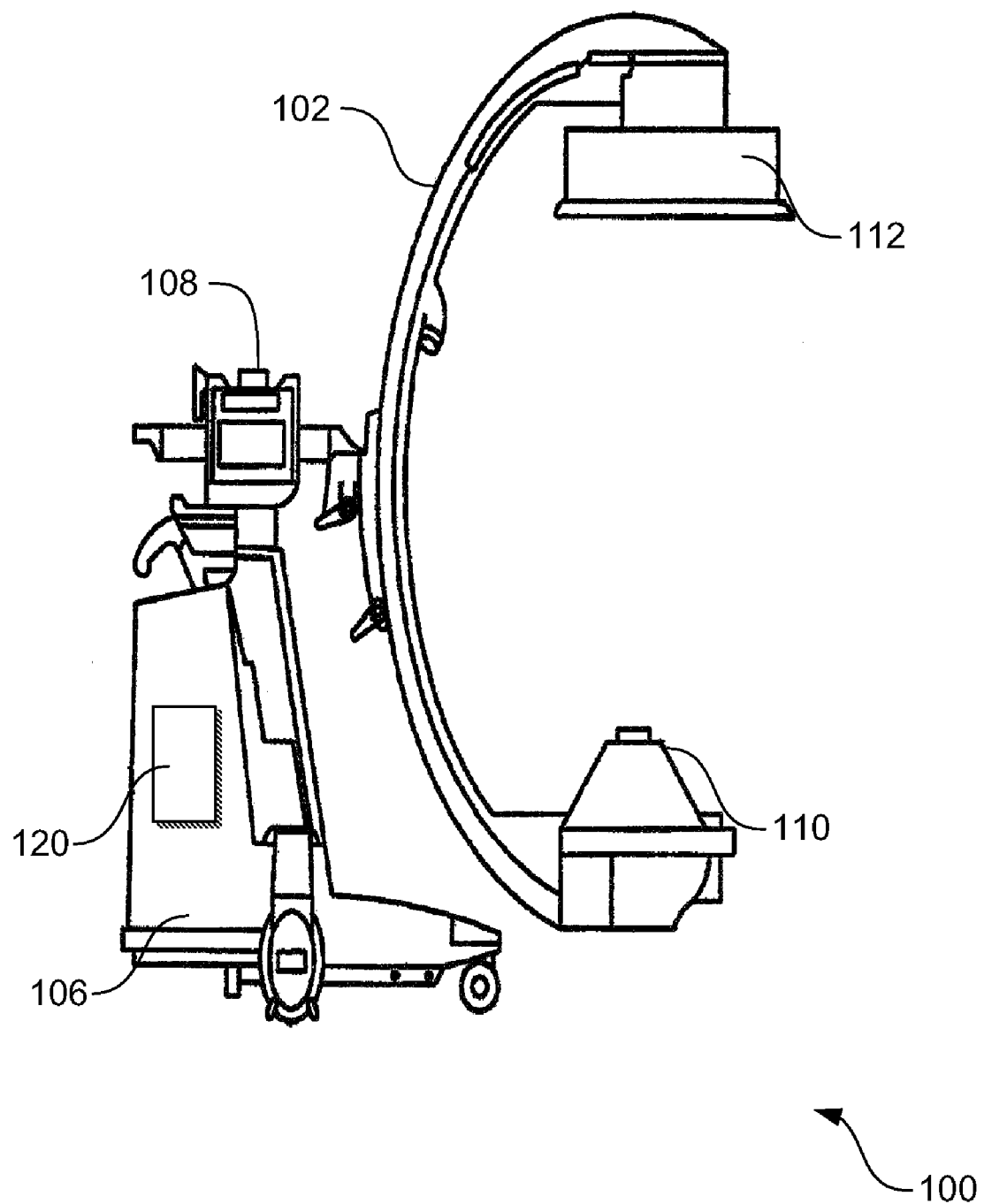
FIG. 1 illustrates an X-ray imaging system having a large digital flat panel detector, in which various embodiments of the present invention may be implemented.

FIG. 1 is a block diagram of an overview of a system to perform medical imaging using an X-ray imaging system. System 100 solves the need in the art for an imaging system that can be utilized to image larger and smaller anatomies with a single X-ray detector.

FIG. 1 illustrates an X-ray imaging system 100 used in accordance with certain embodiments of the present invention. The system 100 includes a mechanism 102, an image detector 112 or X-ray detector 112, an x-ray source 110, a support structure 108, and a wheeled base 106. The image detector 112 and the x-ray source 110 are mounted at opposing locations on the mechanism 102. The support structure 108 provides support for the mechanism 102 and holds the mechanism 102 in a suspended position. The support structure 108 is mounted on a wheeled base 106 that allows the system 100 to be moved.

The support structure 108 provides stable, balanced support for the mechanism 102. The support structure 108 suspends the mechanism 102 for use in imaging a patient or an object. The support structure 108 also allows the mechanism 102 to be rotated about an axis of rotation. This rotation can be accomplished manually or through a motorized mechanism. The support structure 108 is attached to a wheeled base 106 to reposition the X-ray imaging system 100.

The mechanism 102 allows the image detector 112 and the x-ray source 110 to be mounted and positioned about an object to be imaged, such as a patient. The mechanism 102 may be a circular C-shaped or an arc-shaped member, for example. The mechanism 102 enables selective positioning of the image detector 112 and the x-ray source 110 with respect to the width and length of the patient or other object located within the interior free space of the mechanism 102. The image detector 112 may be flat X-ray detector, an image intensifier, or other energy detector for use in imaging an object. The image detector 112 and the x-ray source 110 are mounted at opposing positions on the mechanism 102. The image detector 112 and the x-ray source 110 may be positioned about an object, such as a patient, using mechanism 102 and support structure 108. The image detector 112 and the x-ray source 110 are used to generate a diagnostic image representative of the object being imaged.

In operation, a patient is placed on a table (not shown) that is positioned between the image detector 112 and the x-ray source 110 mounted on mechanisms 102. The support structure 108 moves the mechanism 102. Moving mechanism 102 positions the image detector 112 and the x-ray source 110 at desired locations with respect to the patient. The image detector 112 may be positioned near the patient in order to improve resulting image quality. The imaging process and the operations of the detector 112 and source 110 is accomplished through electronic circuit 120

While the system 100 is not limited to any particular X-ray detector 112, X-ray source 110, or electronic circuits 120, for sake of clarity a simplified block are described.

Figure 2:
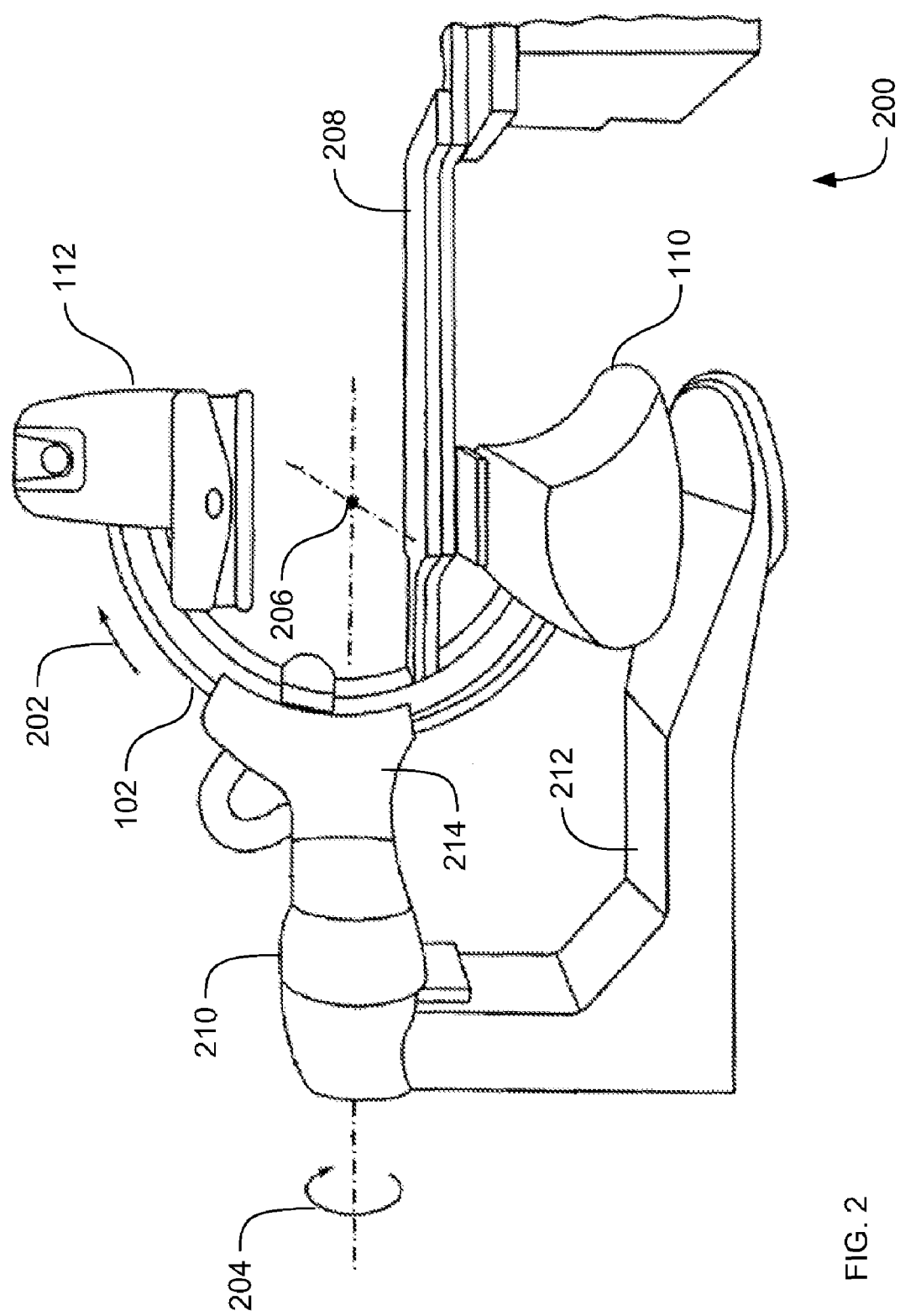
FIG. 2 illustrates a perspective view of an X-ray imaging system according to an embodiment.

FIG. 2 is a block diagram of an overview of a system to perform medical imaging using an X-ray imaging system 200. System 200 solves the need in the art for an imaging system that can be utilized to image larger and smaller anatomies with a single X-ray detector.

Figure 12:
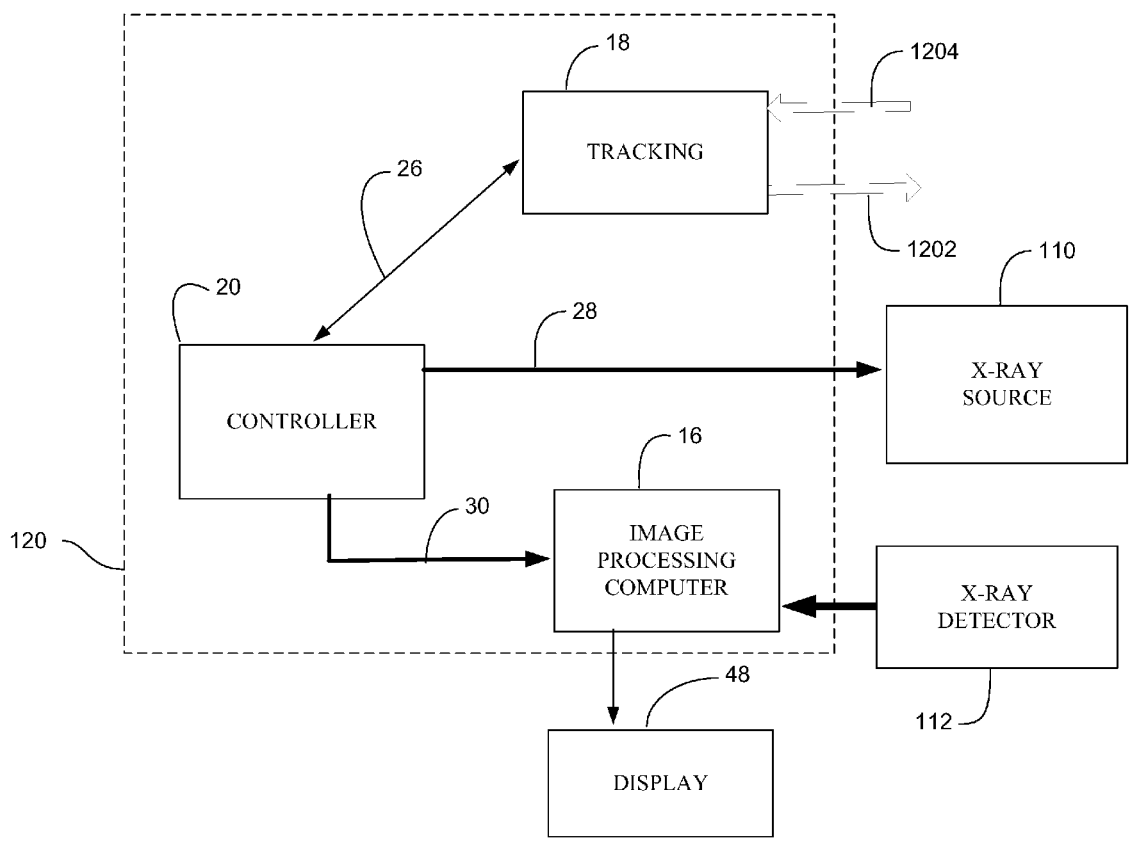
FIG. 12 is a block diagram of a hardware and operating environment in which different embodiments can be practiced.

System 200 includes a mechanism 102, X-ray detector 112, X-ray source 110, and digital processing system (not shown) such as 120 discussed in FIG. 12 for controlling the X-ray detector 112, X-ray source 110, and the imaging process.

System 200 is characterized by a gantry having a mechanism 202 which carries an x-ray source assembly 110 on one of its ends and an x-ray detector array assembly 112 at its other end. The gantry enables the x-ray source 110 and X-ray detector 112 to be oriented in different positions and angles around a patient disposed on a table 208, while enabling a physician access to the patient.

The gantry includes an L-shaped pedestal 212 which has a horizontal leg that extends beneath the table and a vertical leg that extends upward at the end of the horizontal leg that is spaced from of the table 208. In the alternative, system 200 can be supported from a ceiling base through a suspension arm such that the mechanism can freely change the imaging angle with respect to the subject at table 208. A support arm 212 is rotatably fastened to the upper end of vertical leg for rotation about a horizontal pivot axis 204. The pivot axis 204 is aligned with the centerline of the table 208 and the arm 210 extends radially outward from the pivot axis 204 to support a drive assembly 214 on its outer end. The mechanism 102 is slidably fastened to the drive assembly 214 and is coupled to a drive motor (not shown) which slides the mechanism 102 to revolve it about an axis as indicated by arrow 202. The pivot axis 204 and axis intersect each other at an isocenter 206 located above the table 208 and they are perpendicular to each other.

The x-ray source assembly 110 is mounted to one end of the mechanism 102 and the detector array assembly 112 is mounted to its other end. The x-ray source 110 emits a cone beam of x-rays which are directed at the detector array 112. The source/detector assemblies 110 and 112 extend radially inward to the pivot axis 204 such that the center ray of this cone beam passes through the system isocenter 206. The center ray of the cone beam can thus be rotated about the system isocenter around either the pivot axis 204 or the axis, or both during the acquisition of x-ray attenuation data from a subject placed on table 208.

Figure 3:
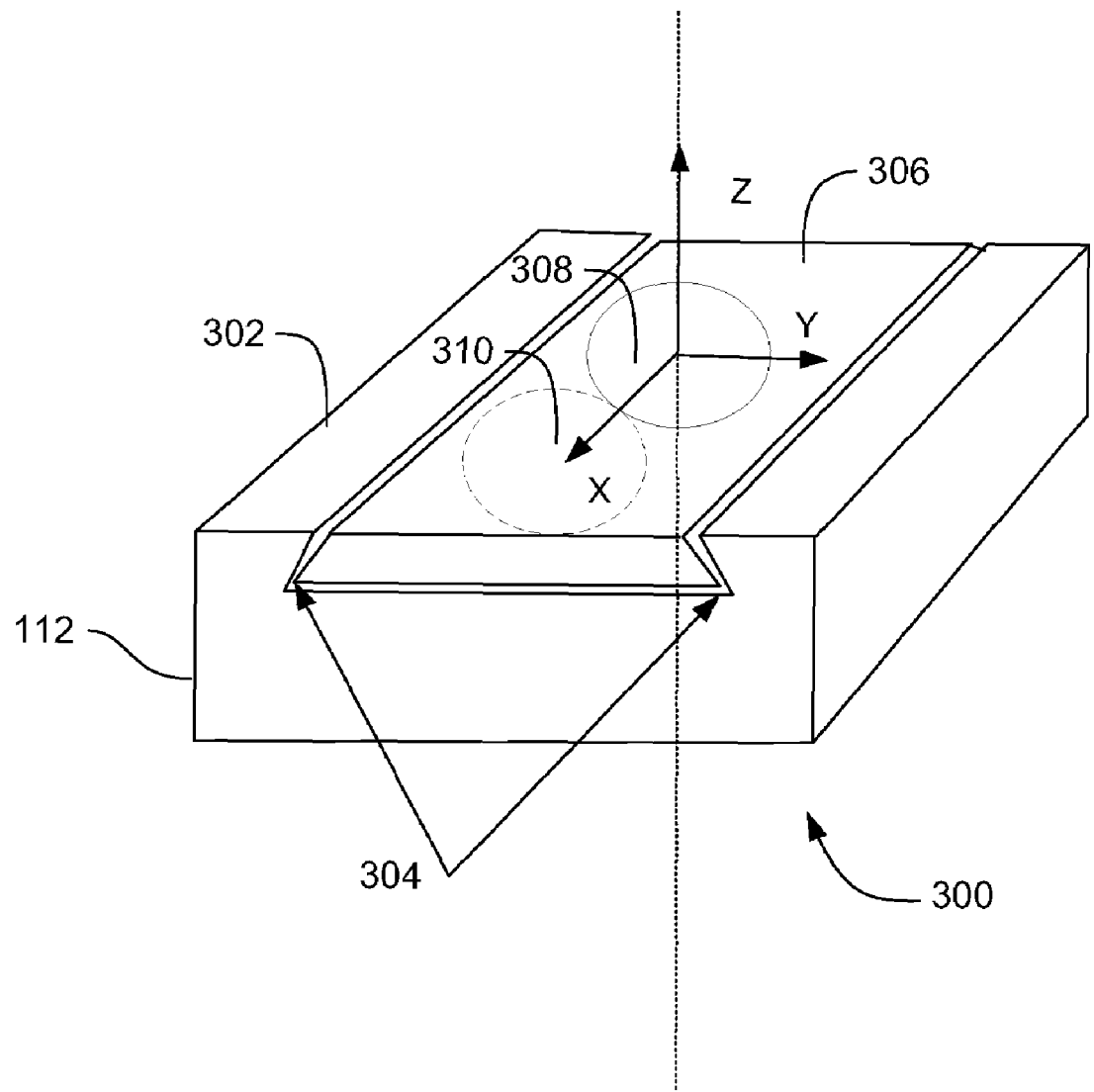
FIG. 3 is a view of an X-ray detector with a movable mount.

FIG. 3 is a block diagram of X-ray detector mount that can shift the detector to perform medical imaging. System 300 solves the need in the art for an X-ray imaging system that can be utilized to image larger and smaller anatomies with a single X-ray detector.

The X-ray detector 112 has a central stage 306 and a detector mount 302. The detector mount 302 includes slides 304 to hold and translate the central stage 306. The slides 304 may be dove tails other structures well known to the mechanical arts. A rail (not shown) can be included so the X-ray detector 112 slide (304) to different positions. The slides 304 have cross-roller bearings so as to avoid the problems of friction and rubbing present in dovetail joints. As the central stage 306 moves in the X-direction the center of the beam field is shifted from its initial position 308 to a position that is closer to the edge of the detector 310.

Figure 4:
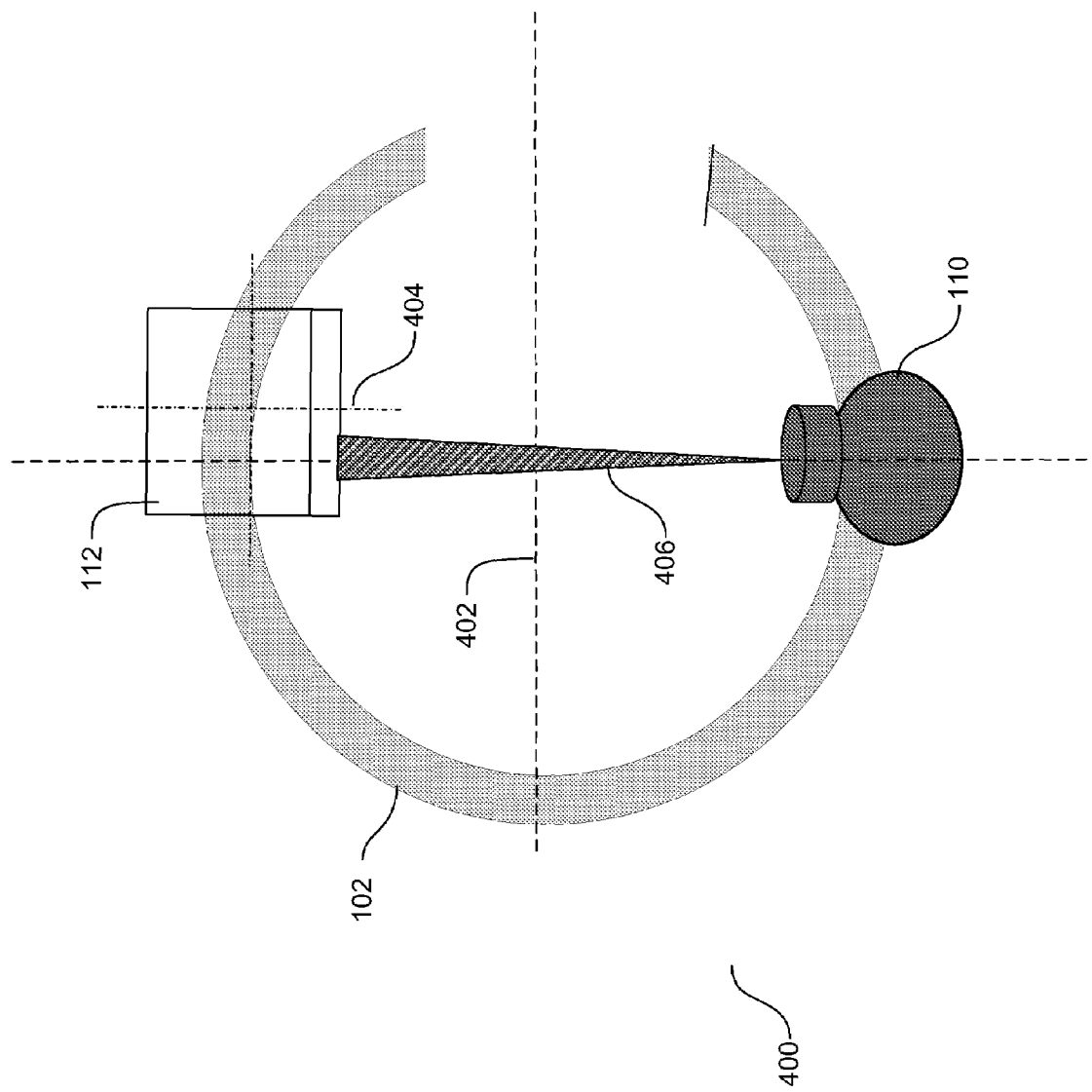
FIG. 4 is a view of a linear shifted X-ray detector according to an embodiment.

FIG. 4 is a representation of a shifted X-ray detector in accordance to an embodiment of the invention. System 400 has a mechanism 102, X-ray detector 112, and X-ray source 110. The beam field 406 emanating from X-ray source 110 runs through the center of rotation 402 of the mechanism 102, which point corresponds to the isocenter of mechanism 102, so that the orbital and angling motions of the mechanism 102 ensue isocentrically. In accordance to an embodiment the X-ray detector 112 is displaced or shifted laterally causing the beam field (FOV) to be defined at the edge of the X-ray detector 112. The displacement involves effectively shifting the sensitive area and x-ray central-beam 406 toward the X-ray detector 112 edge nearest the patient (not shown) during procedures which require reduced-field and high angulations, as during cardiac catheterization, thereby decreasing the space between the edge of the X-ray detector 112 and the patient. Ordinarily, a large X-ray detector 112 would need to be placed far from the patient during longitudinally angulated views, compromising image quality and causing excessive x-ray dose. This would linearly shift the detector in an opposite direction to which it being angled, effectively placing the X-ray detector's 112 sensitive area and x-ray beam 406 at the edge of the X-ray detector 112 which is nearest the patient, while creating no change in beam geometry or centering. In the alternative, instead of moving X-ray detector 112 the shifting mechanism could be placed at the X-ray source 110 and the beam could be re-centered at toward the edge of the X-ray detector 112. The re-centering of the beam on the X-ray detector 112 by shifting the X-ray source 110 would have the advantage of not only allowing the use of large-field detectors for cardiology, but also allowing a lowering of the operational table height during the cardiac procedure.

Figure 5:
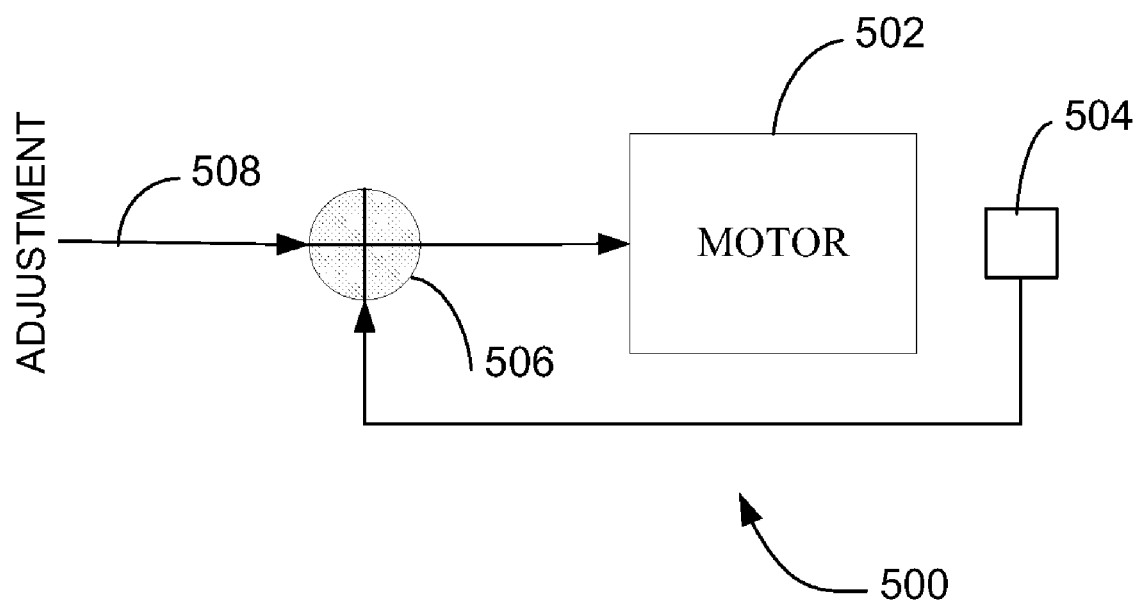
FIG. 5 is a diagram of apparatus, according to an embodiment for regulating an electric motor so as to provide linear shifting of the X-ray detector.

In FIG. 5 a possible arrangement 500 for regulating the shifting of the X-ray detector 112 or the displacing of the X-ray source 110 in accordance to an embodiment. The X-ray imaging system 100 is equipped with an electric power drive 502 for shifting the X-ray detector 112 or X-ray source from position to position and is optionally provided with a speed measuring device 504 that is mounted adjacent rotating motor shaft (not shown). The function of the motor is to move the rails 304 from position to position. The positions could be established device 504 is connected to a combiner 506 through an electrical conductor to provide a source of direct feedback of motor speed to regulate the speed of the motor when combined with an adjustment signal from a controller such as controller 20 in FIG. 2. In some embodiments, the initial speed signal can be set to zero (static) and the speed is regulated by the control signal 508 and the speed measuring device signal from device 504. The control signal could be set to a slow speed giving the operator an indication that the portable detector or X-ray source is in the desired location. In the alternative, the speed measuring device 504 is removed and the speed regulating signals are a combination of the initial speed signal 508 and the adjustment signal 508 from the controller. In some embodiments, only the initial speed signal and the adjustment signal 508 are used to regulate the speed of the electric power drive. The controller for producing the adjustment signal used to regulate the speed of the motor 502 is described with reference to system 120 at FIG. 2.

Figure 6:
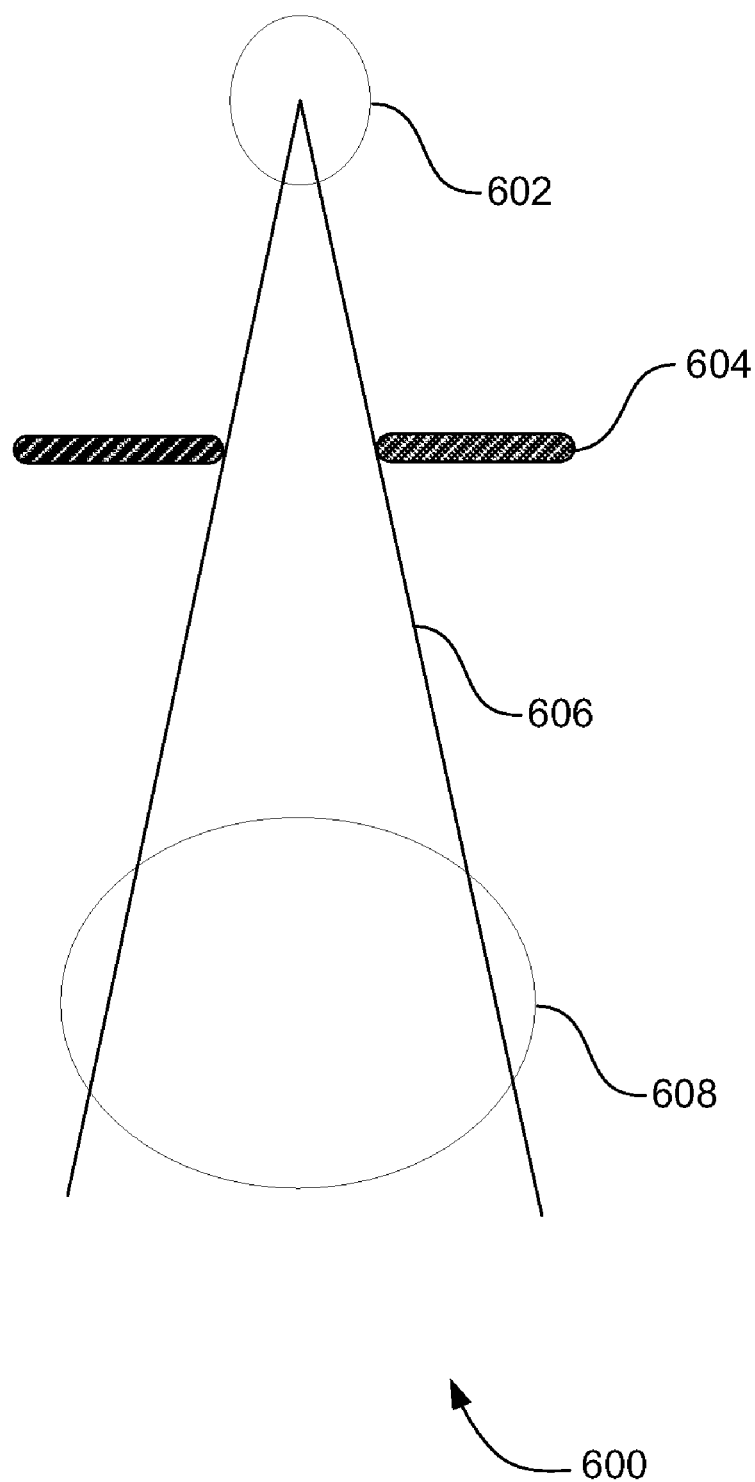
FIG. 6 is a diagram of a collimator for shifting an X-ray beam field.

FIG. 6 is representation of the use of a collimator to shift the beam field 606 from one location to another location in accordance to an embodiment. The radiation source 602 may be any radiation source capable of emitting a suitable radiation 606 such as X-rays, beta rays, or gamma rays. The emitted radiation passes through an aperture of a collimator 604 which embodies the present invention and is applied to an object 608.

Figure 7:
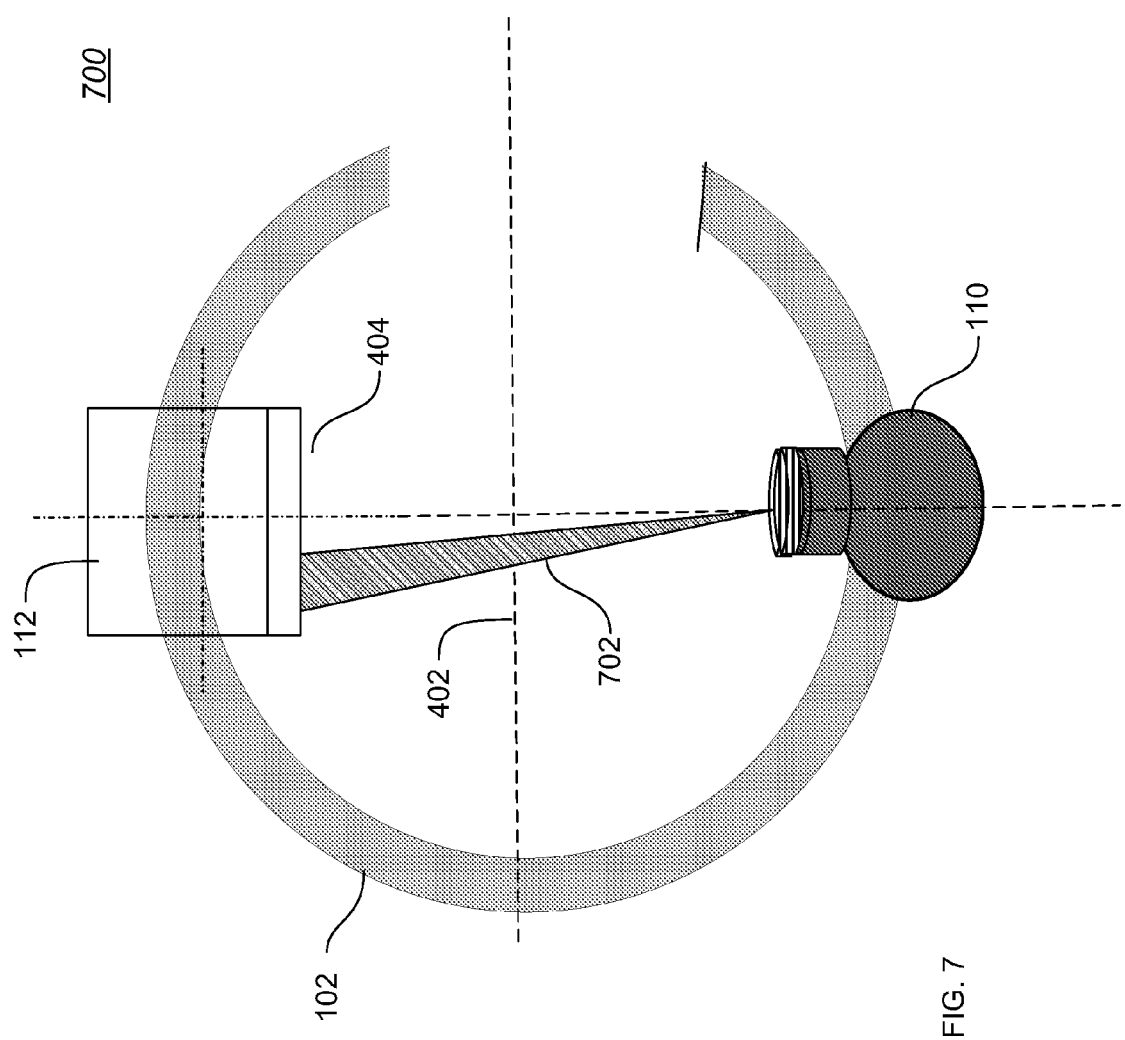
FIG. 7 is a view of a linear shifted X-ray beam field according to an embodiment.

FIG. 7 is a representation of a shifted X-ray detector in accordance to an embodiment of the invention. System 700 has a mechanism 102, X-ray detector 112, and X-ray source 110. It should be noted that the center 404 of the X-ray detector 112 is aligned with the center of rotation of the mechanism 102. The beam field 702 emanating from X-ray source 110 is deflected or shifted away from the center of rotation 402 of mechanism 102, which point corresponds to the isocenter of mechanism 102, so that the orbital and angling motions of the mechanism 102 ensue isocentrically.

In accordance to an embodiment, the beam field 702 is displaced or shifted laterally causing the beam field (FOV) to be defined at the edge of the X-ray detector 112. The shifting of the beam field is accomplished by the collimator arrangement 600 described above with FIG. 6. The displacement involves effectively shifting the x-ray central-beam 402 toward the X-ray detector 112 edge nearest the patient (not shown) during procedures which require reduced-field and high angulations, as during cardiac catheterization, thereby decreasing the space between the edge of the X-ray detector 112 and the patient. It should be noted that one could shift the X-ray tube and the collimator assembly to accomplish the same result. This flexibility is enhanced by the ability to offset the central ray 702 of the x-ray source 110 with respect to the axis 404 of the x-ray detector 112 by displacement of the x-ray source or by offset collimation of the x-ray beam. In either case, when an extreme angulation is required, that beam may be directed to a desired area of the x-ray detector 112 rather than to the center of the x-ray detector 404 and that area preferentially scanned. This capability allows improved positioning with respect to the patient without obstruction by the edges of the detector assembly for large aperture x-ray detectors 112 such as may be desirable in other situations.

The system level overview of the operation of an embodiment is described above in this section of the detailed description. Some embodiments operate in a multi-processing, multi-threaded operating environment on a computer, such as controller 20 in FIG. 2.

In the previous section, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 800-1000 are performed by a program executing on, or performed by firmware or hardware that is a part of, a computer, such as computer or controller 20 in FIG. 2

Figure 8:
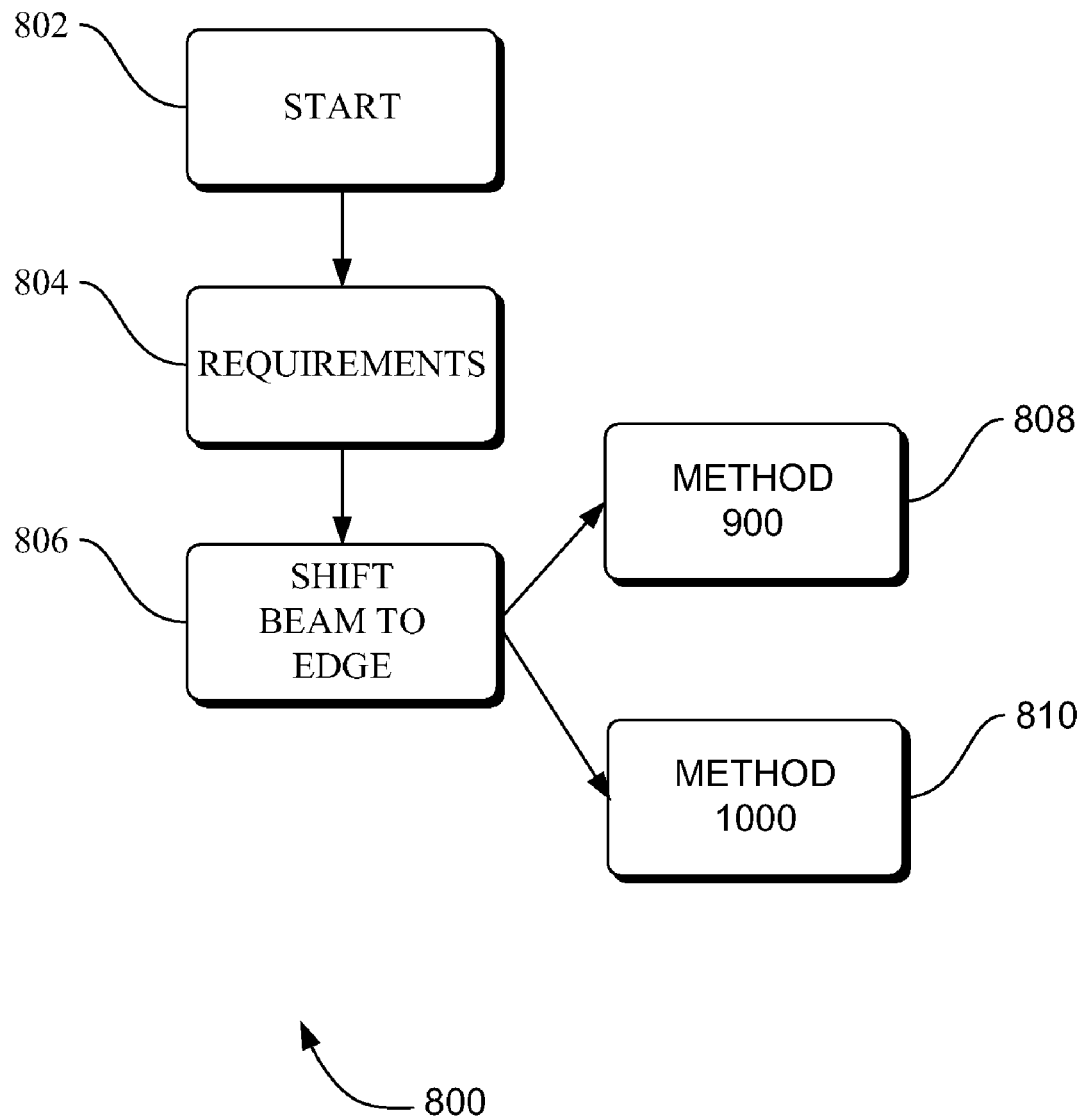
FIG. 8 is a flowchart of a method for angulation enhancement, according to an embodiment.

FIG. 8 is a flowchart of a method 800 for imaging procedures that require reduced field and high angulations, according to an embodiment. Method 800 solves the need in the art for an X-ray imaging system that can be utilized to image larger and smaller anatomies with a single X-ray detector.

Method 800 includes start 802, requirements 804, and shifting beam to edge of detector by either the X-ray detector displacement method 900 or the beam field displacement method 10000.

In action 802 the procedure for operating on the edge of the detector is initiated. The initiation could be caused by the operator selecting or activating a switch. In the alternative, the activation could be initiated automatically by the X-ray imaging system based on an optimization procedure. Once the procedure is initiated control passes action 804 for further processing.

In action 804, the requirement for the X-ray imaging system is generally a need to accommodate reduced-field and high angulations. Additionally, the requirement could be how far from the center of the X-ray detector 112 the field of view (FOV) needs to be within the plane of the X-ray detector. Once the requirements have been received control passes to action 806 for further processing.

In action 806, the process determines which one of the methods to use for causing the beam field to be formed on the edge of the X-ray detector 112. In action 808, a method (900 at FIG. 9) for physically shifting the X-ray detector 112 is used for forming the beam field at the edge of the detector. In action 810, a method (1000 at FIG. 10) is used for forming the beam field by diverting the beam to the edge of the detector.

Figure 9:
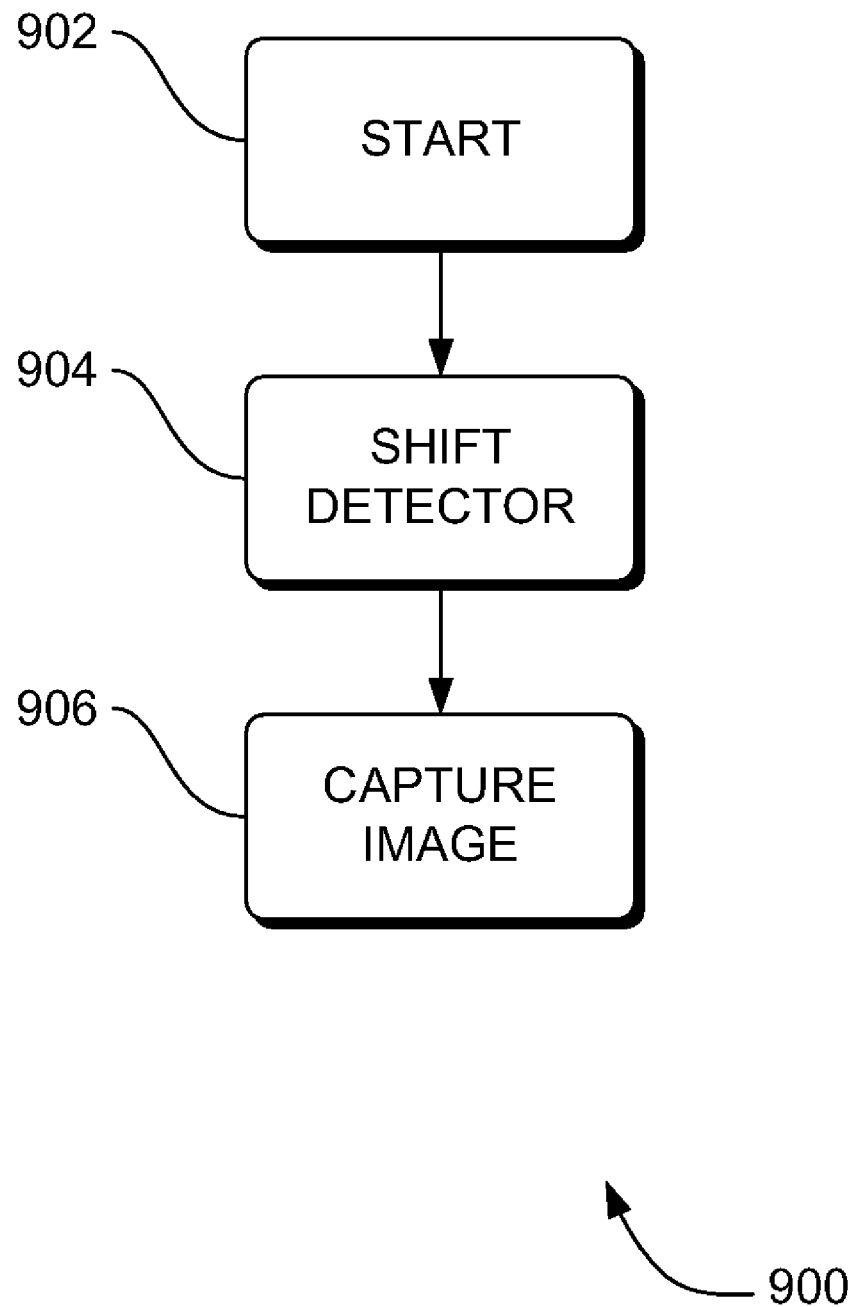
FIG. 9 is a flowchart of a method for angulation enhancement through linear shifting of an X-ray detector, according to an embodiment.

FIG. 9 is a flowchart of a method 900 for imaging procedures that require reduced field and high angulations, according to an embodiment. Method 900 starts by receiving a call from action 806 (FIG. 8) about requirements for how far from the center of the X-ray detector 112 the field of view (FOV) needs to be within the plane of the X-ray detector. The requirement is forwarded to action 904 for further processing.

In action 904, the X-ray detector 112 is shifted. The shifting of the X-ray detector is a shift or displacement of the X-ray detector 112 by sliding the X-ray detector on rails. The motorized arrangement 500 (FIG. 5) can be used in conjunction with controller 20 (FIG. 2) to move the detector laterally along the slides 304. Once the X-ray detector 112 has been positioned in the desired location control passes to action 906.

In action, 906 the image is captured and control is returned to the main medical imaging routine for applying imaging processing techniques on the acquired image data.

Figure 10:
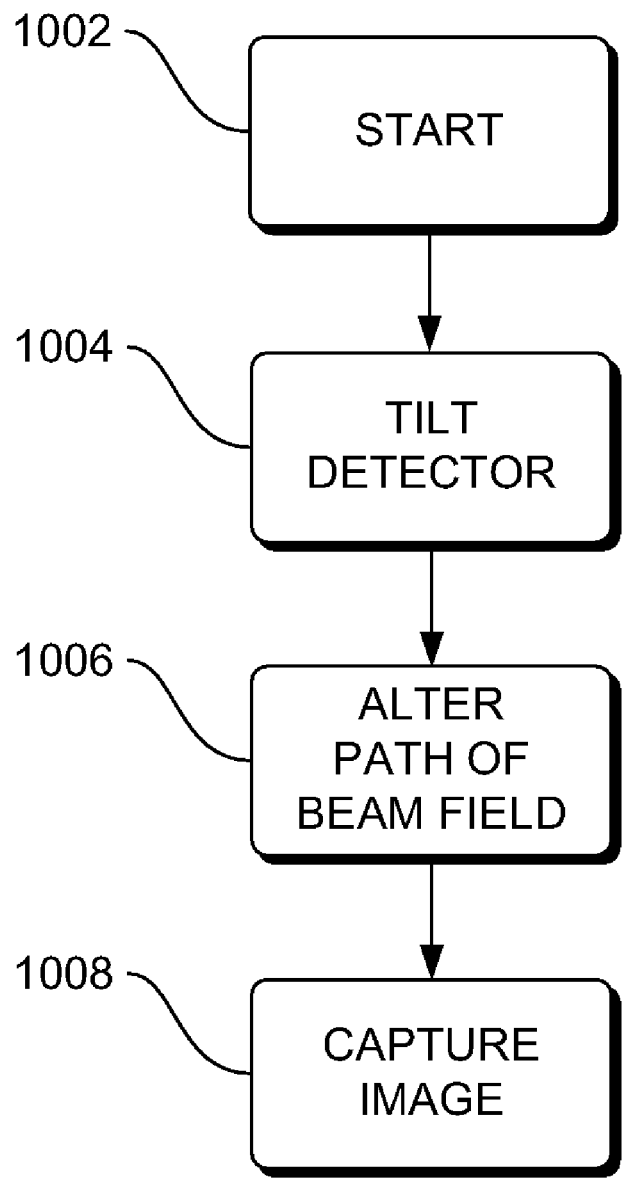
FIG. 10 is a flowchart of a method for angulation enhancement through beam field shifting, according to an embodiment.

FIG. 10 is a flowchart of a method 1000 for imaging procedures that require reduced field and high angulations, according to an embodiment. Method 1000 starts by receiving a call from action 806 (FIG. 8) about requirements for how far from the center of the X-ray detector 112 the field of view (FOV) needs to be within the plane of the X-ray detector. While method 900 displaces the detector, method 1000 displaces the beam field by an amount that would cause the edge of the detector to form the beam field. After receiving the call control passes to action 1004 for further processing.

In action 1004, the X-ray detector 112 is tilted to accommodate possible geometric distortions of the beam field. In action 1006, the path of the beam field is altered by the collimator. The function of the collimator 600 is to define the shape and size of the x-ray stream and to rotate the shape of the x-ray stream while possibly varying the size of the x-ray stream, for example, to ensure that no x-rays fall outside the chosen area of the x-ray detector 112. After the x-ray stream passes through the collimator 604 the x-ray stream may pass through any matter, such as body tissue, organs and/or bones, which exists between the collimator and the x-ray detector 112. The x-ray detector may then tilt so that it will fit in a visual display that the x-ray image is output.

In action 1008, the beam field is position on the edge of X-ray detector 112 and control is returned to the main medical imaging routine for applying imaging processing techniques on the acquired image data.

Figure 11:
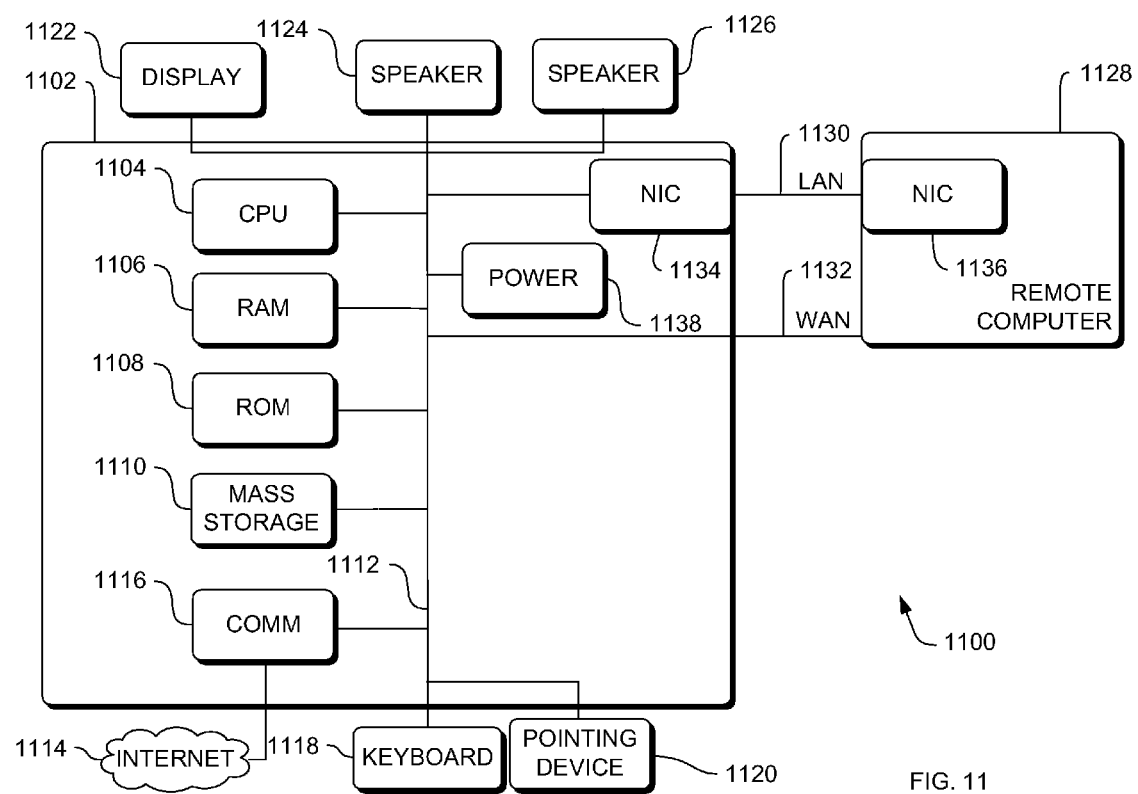
FIG. 11 is a block diagram of hardware and operating environment in which different embodiments can be practiced.

In some embodiments, methods 800-1000 are implemented as a computer data signal embodied in a carrier wave, that represents a sequence of instructions which, when executed by a processor, such as processor 1104 in FIG. 11, cause the processor to perform the respective method. In other embodiments, methods 800-1000 are implemented as a computer-accessible medium having executable instructions capable of directing a processor, such as processor 1104 in FIG. 11, to perform the respective method. In varying embodiments, the medium is a magnetic medium, an electronic medium, or an optical medium.

Hardware and Operating Environment

FIG. 11 is a block diagram of a hardware and operating environment 1100 in which different embodiments can be practiced. Hardware and operating environment 1100 can be a substitute for or operate in conjunction with controller 20 of FIG. 2. The description of FIG. 11 provides an overview of computer hardware and a suitable computing environment in conjunction with which some embodiments can be implemented. Embodiments are described in terms of a computer executing computer-executable instructions. However, some embodiments can be implemented entirely in computer hardware in which the computer-executable instructions are implemented in read-only memory. Some embodiments can also be implemented in client/server computing environments where remote devices that perform tasks are linked through a communications network. Program modules can be located in both local and remote memory storage devices in a distributed computing environment.

Computer 1102 includes a processor 1104, commercially available from Intel, Motorola, Cyrix and others. Computer 1102 also includes random-access memory (RAM) 1106, read-only memory (ROM) 1108, and one or more mass storage devices 1110, and a system bus 1112, that operatively couples various system components to the processing unit 1104. The memory 1106, 1108, and mass storage devices, 1110, are types of computer-accessible media. Mass storage devices 1110 are more specifically types of nonvolatile computer-accessible media and can include one or more hard disk drives, floppy disk drives, optical disk drives, and tape cartridge drives. The processor 1104 executes computer programs stored on the computer-accessible media.

Computer 1102 can be communicatively connected to the Internet 1114 via a communication device 1116. Internet 1114 connectivity is well known within the art. In one embodiment, a communication device 1116 is a modem that responds to communication drivers to connect to the Internet via what is known in the art as a "dial-up connection." In another embodiment, a communication device 1116 is an Ethernet® or similar hardware network card connected to a local-area network (LAN) that itself is connected to the Internet via what is known in the art as a "direct connection" (e.g., T1 line, etc.).

A user enters commands and information into the computer 1102 through input devices such as a keyboard 1118 or a pointing device 1120. The keyboard 1118 permits entry of textual information into computer 1102, as known within the art, and embodiments are not limited to any particular type of keyboard. Pointing device 1120 permits the control of the screen pointer provided by a graphical user interface (GUI) of operating systems such as versions of Microsoft Windows®. Embodiments are not limited to any particular pointing device 1120. Such pointing devices include mice, touch pads, trackballs, remote controls and point sticks. Other input devices (not shown) can include a microphone, joystick, game pad, satellite dish, scanner, or the like.

In some embodiments, computer 1102 is operatively coupled to a display device 1122. Display device 1122 is connected to the system bus 1112. Display device 1122 permits the display of information, including computer, video and other information, for viewing by a user of the computer. Embodiments are not limited to any particular display device 1122. Such display devices include cathode ray tube (CRT) displays (monitors), as well as flat panel displays such as liquid crystal displays (LCD's). In addition to a monitor, computers typically include other peripheral input/output devices such as printers (not shown). Speakers 1124 and 1126 provide audio output of signals. Speakers 1124 and 1126 are also connected to the system bus 1112.

Computer 1102 also includes an operating system (not shown) that is stored on the computer-accessible media RAM 1106, ROM 1108, and mass storage device 1110, and is executed by the processor 1104. Examples of operating systems include Microsoft Windows®, Apple MacOS®, Linux®, UNIX®. Examples are not limited to any particular operating system, however, and the construction and use of such operating systems are well known within the art.

Embodiments of computer 1102 are not limited to any type of computer 1102. In varying embodiments, computer 1102 comprises a PC-compatible computer, a MacOS®-compatible computer, a Linux®-compatible computer, or a UNIX®-compatible computer. The construction and operation of such computers are well known within the art.

Computer 1102 can be operated using at least one operating system to provide a graphical user interface (GUI) including a user-controllable pointer. Computer 1102 can have at least one web browser application program executing within at least one operating system, to permit users of computer 1102 to access an intranet, extranet or Internet world-wide-web pages as addressed by Universal Resource Locator (URL) addresses. Examples of browser application programs include Netscape Navigator® and Microsoft Internet Explorer®.

The computer 1102 can operate in a networked environment using logical connections to one or more remote computers, such as remote computer 1128. These logical connections are achieved by a communication device coupled to, or a part of, the computer 1102. Embodiments are not limited to a particular type of communications device. The remote computer 1128 can be another computer such as controller 20 of FIG. 12, a server, a router, a network PC, a client, a peer device such as electronic device 120 or other common network node. The logical connections depicted in FIG. 11 include a local-area network (LAN) 1130 and a wide-area network (WAN) 1132. Such networking environments are commonplace in offices, enterprise-wide computer networks, intranets, extranets and the Internet.

When used in a LAN-networking environment, the computer 1102 and remote computer 1128 are connected to the local network 1130 through network interfaces or adapters 1134, which is one type of communications device 1116. Remote computer 1128 also includes a network device 1136. When used in a conventional WAN-networking environment, the computer 1102 and remote computer 1128 communicate with a WAN 1132 through modems (not shown). The modem, which can be internal or external, is connected to the system bus 1112. In a networked environment, program modules depicted relative to the computer 1102, or portions thereof, can be stored in the remote computer 1128.

Computer 1102 also includes power supply 1138. Each power supply can be a battery.

FIG. 12 is a block diagram that provides a system level overview of an electronic controlling system 120. Embodiments are described as operating in a multi-processing, multi-threaded operating environment on a computer.

The electronic system is electrically connected to an X-ray generator 110, X-ray detector 112, and a tracking subsystem 18. A controller 20 communicates directly with an X-ray generator 14, image processor 16, video subsystem (not shown), and input/output devices (not shown). The image processor 16 communicates with a display 48 and other data processing devices. The imaging apparatus 100 or 200 includes an X-ray source 110 mounted to one side and an X-ray detector 112 mounted to the opposed side. The imaging apparatus 100 is movable in several directions along multiple image acquisition paths such as an orbital tracking direction, longitudinal tracking direction, lateral tracking direction, transverse tracking direction, pivotal tracking direction, and wig-wag tracking direction.

The tracking subsystem 18 monitors the position of a patient, the detector 112, and an instrument or tool used by a medical professional during a diagnostic or interventional surgical procedure. The tracking subsystem 18 provides tracking component coordinates with respect to each of the patient, detector 112, and instrument that report data or information to controller 20. This data can be routed to the controller 20 through input lines 1204. The controller 20 can communicate to dedicated devices through output line 1202. The controller 20 uses the tracking component coordinates 26 to continuously calculate the positions of the detector 112, patient, and instrument with respect to a coordinate system defined relative to a coordinate system reference point. The reference point for the coordinate system is dependent, in part, upon the type of tracking subsystem used. The controller 20 sends control or trigger commands 28 to the X-ray source 110 that in turn causes one or more exposures to be taken by the X-ray detector 112. The controller 20 provides exposure reference data to the image processor 16. The control or trigger commands 28 and exposure reference data 30 are generated by the controller 20, as explained in more detail below, based on the tracking component coordinates 26 as the imaging apparatus is moved along an image acquisition path.

By way of example, the imaging apparatus 12 may be manually moved between a first and second positions (P1, P2) as a series of exposures are obtained. The image acquisition path may be along the orbital rotation direction and the detector 112 may be rotated through a range of motion from zero (0) to 145 degrees or from 0 to 190 degrees.

The image processor 16 collects a series of image exposures from the X-ray detector 112 as the X-ray imaging system 100 is rotated. The X-ray detector 112 collects an image exposure each time the X-ray source 110 is triggered by the controller 20. The image processor 16 combines each image exposure 32 with corresponding exposure reference data 30 and uses the exposure reference data 30 to construct a three-dimensional volumetric data set. The three-dimensional volumetric data set is used to generate images, such as slices, of a region of interest from the patient. For instance, the image processor 16 may produce from the volumetric data set saggital, coronal and/or axial views of a patient heart, lungs, veins, spine, knee, and the like.

The tracking subsystem 18 receives position information from X-ray detector 112, patient and instrument position sensors (not shown), respectively. The sensors may communicate with the tracking subsystem 18 via hardwired lines, infrared, wireless or any known or to be discovered method for scanning sensor data 1204 and 1202. The sensors and tracking subsystem 18 may be configured to operate based on one or more communication medium such as electromagnetic, optics, or infrared. It is well know to those in the art to use an electromagnetic (EM) implementation with field transmitter/generator to provide with up to three orthogonally disposed magnetic dipoles. The magnetic fields generated by each of these dipoles are distinguishable or ID from one another through phase, frequency or time division multiplexing. The magnetic fields may be relied upon for position detection. The field transmitter/generator may form any one of the patient position sensor, detector position sensor or instrument position sensor. The field transmitter/generator emits EM fields that are detected by the other two of the position sensors. By way of example, the patient position sensor may comprise the field transmitter/generator, while the detector and instrument position sensors and comprise one or more field sensors each.

The sensors and tracking subsystem 18 may be configured based on optical or infrared signals. A position monitoring camera can be added to monitor the position of the sensors and to communicate with the tracking subsystem 18. An active infrared light may be periodically emitted by each sensor and detected by the position monitoring camera (not shown). Alternatively, the sensors may operate in a passive optical configuration, whereby separate infrared emitters are located at the camera and/or about the room. The emitters are periodically triggered to emit infrared light. The emitted infrared light is reflected from the sensors onto one or more cameras. The active or passive optical information collected through the cooperation of the sensors and position monitoring camera is used by the tracking subsystem 18 define tracking component coordinates for each of the patient, detector 112 and instrumentation. The position information may define six degrees of freedom, such as x, y, z coordinates and pitch, roll and yaw angular orientations. The position information may be defined in the polar or Cartesian coordinate systems.

Notwithstanding the communication medium used, the tracking subsystem 18 generates a continuous stream of tracking component coordinates, such as the Cartesian coordinates, pitch, roll and yaw for the instrument (I(x, y, z, pitch, roll, yaw)), for the detector 112 D(x, y, z, pitch, roll, yaw), and/or patient P(x, y, z, pitch, roll, yaw). When the patient position sensor is provided with an EM transmitter therein, the coordinate reference system may be defined with the origin at the location of the patient position sensor. When an infrared tracking system is used, the coordinate system may be defined with the point of origin at the patient monitoring camera.

The controller 20 continuously collects the stream of tracking component coordinates and continuously calculates the position of the patient, detector 112 and instrument relative to a reference point. The controller 20 may calculate rotation positions of the imaging apparatus and store each such position temporarily. Each new rotation position may be compared with a target position, representing a fixed angular position or based on a fixed accurate movement. When a 3-D acquisition procedure is initiated, the controller 20 establishes a reference orientation for the imaging apparatus 100. For instance, the controller 20 may initiate an acquisition process once the detector 112 is moved to one end of an image acquisition path with beginning and ending points corresponding to a 0 degree angle and 190 degree angle, respectively. Alternatively, the controller 20 may initialize the coordinate reference system with the imaging apparatus 100 located at an intermediate point along its range of motion. In this alternative embodiment, the controller 20 defines the present position of the detector 112 as a starting point for an acquisition procedure. Once the controller 20 establishes the starting or initial point for the image acquisition procedure, a control or trigger command 28 is sent to the X-ray source 110 and initial exposure reference data 30 is sent to the image processor 16. An initial image exposure is obtained and processed.

After establishing an initial position for the X-ray detector 112, the controller 20 continuously monitors the tracking component coordinates for the X-ray detector 112 and determines when the X-ray detector 112 moves a predefined distance. When the tracking component coordinates indicate that the X-ray detector 112 has moved the predefined distance from the initial position, the controller 20 sends a new control or trigger command 28 to the X-ray source 110 thereby causing the X-ray source 110 to take an X-ray exposure. The controller 20 also sends new exposure reference data 30 to the image processor 16. This process is repeated at predefined intervals over an image acquisition path to obtain a series of images. The image processor 16 obtains the series of image exposures that correspond to a series of exposure reference data 30 and combines the data into a volumetric data set that is stored in memory.

The controller 20 may cause the X-ray source 110 and image processor 16 to obtain image exposures at predefined arc intervals during movement of the X-ray detector 112 around the orbital path of motion. The orbital range of motion for the detector 112, over which images are obtained, may be over a 145 degree range of motion or up to a 190 degree range of motion for the imaging apparatus 100. Hence, the X-ray detector 112 may be moved from a zero angular reference point through 145 degree of rotation while image exposures are taken at predefined arc intervals to obtain a set of image exposures used to construct a 3-D volume. Optionally, the arc intervals may be evenly spaced apart at 1 degree, 5 degree, 10 degree and the like, such that approximately 100, 40, or 15, respectively, image exposures or frames are obtained during movement of the detector 112 through rotation. The arc intervals may be evenly or unevenly spaced from one another. In the alternative, the operator at any desired speed may manually move the detector 112. The operator may also move the detector 112 at an increasing, decreasing, or at a variable velocity since exposures are triggered only when the detector 112 is located at desired positions that are directly monitored by the tracking subsystem 18. Integrated within the X-ray imaging system and navigation system 100 is the video subsystem (not shown) for capturing, recording, storing and replaying full resolution video of procedures occurring on the imaging and navigation system. The video subsystem is coupled to image processor 16, tracking subsystem 18, and controller 20.

A method and apparatus is described. A technical effect of the method and apparatus is to have a large X-ray detector on a vascular X-ray imaging system be utilized to image smaller anatomy at extreme angles. Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

I claim:

1. An X-ray imaging system for angulation enhancement, the system comprising:
    an X-ray detector having a plane, wherein the X-ray detector is mounted to one end of the X-ray imaging system, the X-ray detector having a central stage and a detector mount, the detector mount including at least one slide to hold and translate the central stage, each of the at least one slide having at least one cross-roller bearing;
    an X-ray source disposed to project an X-ray beam into the plane to define a beam field therein, wherein the X-ray source is mounted to the opposite end of the X-ray imaging system, and as the central stage moves in a direction, a center of the beam field is shifted from an initial position to a position that is closer to the edge of the detector; and
    an apparatus operable to shift the beam field towards an edge of the X-ray detector in order to achieve angulation requirements.

2. The X-ray system of claim 1, wherein the X-ray detector is a flat X-ray detector.

3. The X-ray system of claim 2, wherein the X-ray detector is arranged on one or more rails.

4. The X-ray system of claim 3, wherein the apparatus operable to shift the beam field further comprises:
    a control unit for displacing the X-ray source by linearly shifting the X-ray source relative to the X-ray detector so as to define the beam field towards an edge of the X-ray detector.

5. The X-ray system of claim 3, wherein the apparatus operable to shift the beam field further comprises:
a control unit for controlling the position of the X-ray detector by linearly shifting the X-ray detector relative to the X-ray source so as to define the beam field towards an edge of the X-ray detector.

6. The X-ray system of claim 2, wherein the apparatus operable to shift the beam field further comprises:
a collimator for altering beam path so as to confine the beam towards an edge of the X-ray detector.

7. The X-ray system of claim 6, wherein the X-ray detector is arranged on a tilt mechanism.

8. The X-ray system of claim 7, wherein the apparatus operable to shift the beam field further comprises:
a control unit for controlling the tilt of the X-ray detector and altering the path of the beam through the collimator so as to define the beam field towards an edge of the X-ray detector.

9. A method for controlling an X-ray imaging system to provide angulation enhancement, the method comprising:
providing an X-ray detector positioned at one end of the X-ray imaging system;
projecting an X-ray beam onto the X-ray detector so as to define a beam field at the X-ray detector;
shifting the beam field towards an edge of the X-ray detector, the X-ray detector having a central stage and a detector mount, the detector mount including at least one slide to hold and translate the central stage, each of the at least one slide having at least one cross-roller bearing, and as the central stage moves in a direction, a center of the beam field is shifted from an initial position to a position that is closer to the edge of the detector in order to achieve angulation requirements.

10. The method of claim 9, wherein the X-ray detector is a flat X-ray detector.

11. The method of claim 10, wherein the X-ray detector is arranged on one or more rails.

12. The method of claim 11, wherein shifting the beam is controlling the position of the X-ray detector by linearly shifting the X-ray detector relative to a X-ray source so as to define the beam field towards an edge of the X-ray detector.

13. The method of claim 11, wherein shifting the beam is displacing the X-ray source by linearly shifting the X-ray source relative to the X-ray detector so as to define the beam field towards an edge of the X-ray detector.

14. The method of claim 10, wherein the method further comprises:
providing a collimator for altering beam path so as to confine the beam towards an edge of the X-ray detector.

15. The method of claim 14, wherein the X-ray detector is arranged on a tilt mechanism.

16. The method of claim 15, wherein shifting the beam field is controlling the tilt of the X-ray detector and altering the path of the beam through the collimator so as to define the beam field towards an edge of the X-ray detector.

17. An apparatus for imaging comprising:
an X-ray detector having a plane, wherein the X-ray detector is mounted to one end of an X-ray imaging system, the X-ray detector having a central stage and a detector mount, the detector mount including at least one slide to hold and translate the central stage, each of the at least one slide having at least one cross-roller bearing;
an X-ray source disposed to project an X-ray beam into the plane to define a beam field therein, wherein the X-ray source is mounted to the opposite end of the X-ray imaging system, and as the central stage moves in a direction, a center of the beam field is shifted from an initial position to a position that is closer to the edge of the detector;
a processor;
a storage device coupled to the processor; and
an apparatus operative on the processor for:
shifting the beam field towards an edge of the X-ray detector in order to achieve angulation requirements.

18. The apparatus of claim 17, wherein the X-ray detector is a flat X-ray detector.

19. The apparatus of claim 18, wherein the X-ray detector is arranged on one or more rails.

20. The apparatus of claim 17, wherein the apparatus operable to shift the beam field further comprises:
a control unit for controlling the position of the X-ray detector by linearly shifting the X-ray detector relative to the X-ray source so as to define the beam field towards an edge of the X-ray detector.

21. The apparatus of claim 19, wherein the apparatus operable to shift the beam field further comprises:
a control unit for displacing the X-ray source by linearly shifting the X-ray source relative to the X-ray detector so as to define the beam field towards an edge of the X-ray detector.

22. The apparatus of claim 17, wherein the apparatus operable to shift the beam field further comprises:
a collimator for altering beam path so as to confine the beam towards an edge of the X-ray detector.

23. The apparatus of claim 22, wherein the X-ray detector is arranged on a tilt mechanism; and wherein shifting the beam field is controlling the tilt of the X-ray detector and altering the path of the beam through the collimator so as to define the beam field towards an edge of the X-ray detector.

* * * * *